United States Patent
Granger et al.

(10) Patent No.: US 12,144,794 B2
(45) Date of Patent: Nov. 19, 2024

(54) USE OF CAPRYLIC AND CAPRIC TRIGLYCERIDES FOR THE TREATMENT OF A DISEASE OR CONDITION MEDIATED BY FILAGGRIN OR COLLAGEN DEFICIENCY

(71) Applicant: ISDIN, S.A., Barcelona (ES)

(72) Inventors: Corinne Jeanne Rose Granger, Barcelona (ES); Carlos Ramon Trullas Cabanas, Barcelona (ES)

(73) Assignee: ISDIN, S.A., Barcelona (ES)

( * ) Notice: Subject to any disclaimer, the term of this patent is extended or adjusted under 35 U.S.C. 154(b) by 727 days.

(21) Appl. No.: 17/436,231

(22) PCT Filed: Mar. 5, 2020

(86) PCT No.: PCT/EP2020/055846
§ 371 (c)(1),
(2) Date: Sep. 3, 2021

(87) PCT Pub. No.: WO2020/178385
PCT Pub. Date: Sep. 10, 2020

(65) Prior Publication Data
US 2022/0175712 A1 Jun. 9, 2022

(30) Foreign Application Priority Data

Mar. 6, 2019 (EP) .................................... 19382169

(51) Int. Cl.
| | | |
|---|---|---|
| *A61K 31/23* | (2006.01) |
| *A61K 31/05* | (2006.01) |
| *A61K 31/375* | (2006.01) |
| *A61K 31/4045* | (2006.01) |
| *A61K 9/00* | (2006.01) |

(52) U.S. Cl.
CPC .............. *A61K 31/23* (2013.01); *A61K 31/05* (2013.01); *A61K 31/375* (2013.01); *A61K 31/4045* (2013.01); *A61K 9/0014* (2013.01)

(58) Field of Classification Search
CPC ...... A61K 31/23; A61K 31/05; A61K 31/375; A61K 31/4045; A61K 9/0014
USPC .......................................................... 514/522
See application file for complete search history.

(56) References Cited

U.S. PATENT DOCUMENTS 9,452,129 B1    9/2016  Samuel et al.

FOREIGN PATENT DOCUMENTS

| CN | 103340813 B | 7/2014 |
| DE | 202006017031 U1 | 2/2007 |
| EP | 2210588 A1 | 7/2010 |
| WO | WO 2004/000242 A1 | 12/2003 |
| WO | WO 2017/175126 A1 | 10/2017 |

OTHER PUBLICATIONS

International Search Report and Written Opinion mailed May 4, 2020 for International Application No. PCT/EP2020/055846, 20 pages.

*Primary Examiner* — Kristin A Vajda
(74) *Attorney, Agent, or Firm* — Squire Patton Boggs (US) LLP

(57) ABSTRACT

The present invention relates to the use of caprylic and capric triglycerides, a combination of caprylic and capric triglycerides and melatonin or a derivative thereof or a composition containing the caprylic and capric triglycerides alone or in combination with melatonin or a derivative thereof for the treatment of a disease or condition mediated by a filaggrin or collagen deficiency.

17 Claims, No Drawings ized or by an increased degradation of these proteins.
USE OF CAPRYLIC AND CAPRIC TRIGLYCERIDES FOR THE TREATMENT OF A DISEASE OR CONDITION MEDIATED BY FILAGGRIN OR COLLAGEN DEFICIENCY This application is a national-phase filing under 35 U.S.C. § 371 of International Application No. PCT/EP2020/055846 (filed on Mar. 5, 2020), which claims the benefit of European Patent Application No. EP 19382169.1 (filed on Mar. 6, 2019).

The present invention relates to the use of caprylic and capric triglycerides, a combination of caprylic and capric triglycerides and melatonin or a derivative thereof or a composition containing them for the treatment of a disease or condition mediated by a deficiency of filaggrin or collagen

BACKGROUND ART

Disorders of the matrix components of fibroblasts and keratinocytes have been identified as one of the main causes of common skin conditions as well as some connective tissue disorders. A deficiency of the amounts of filaggrin protein and/or collagen can be caused by an abnormal production or by an increased degradation of these proteins.

On one hand, filaggrin is a filament-associated protein that binds to keratin fibres in epithelial cells having a key role in epidermal barrier function. This protein is also a major component of the protein-lipid cornified envelope of the epidermis important for water permeability and blocking the entry of microbes and allergens. Therefore, filaggrin is essential for the regulation of epidermal homeostasis.

Individuals with a deficiency of the amounts of filaggrin are strongly predisposed to suffer from skin diseases such dry skin, ichthyosis vulgaris, and/or eczema. These skin diseases are characterized by hyperlinearity, keratosis pilaris, itchy, scaly and often inflamed skin. Unfortunately, it is not possible to cure filaggrin deficiency or take filaggrin supplements. There are only some measures to try to restore the amount of filaggrin in the skin. Some of these measures involve avoiding soaps, detergents, shampoos and abrasive cleaners and/or increasing the use of emollients.

On the other hand, collagen is a protein found in the skin that gives the skin the appearance of fullness and smoothness. In addition, it sustains internal organs, muscles, tendons, cartilage, and is also present in teeth. Collagen makes up 25% of the whole amount of proteins in the body. There are about 20 different types of collagen in the body. Each group of collagen has vital roles in many of the body's functions, such as formation and maintaining of internal organs. In particular, type III collagen is a fibrillar collagen that consists of only one collagen α chain which is secreted by fibroblasts and other mesenchymal cell types. In particular, type III collagen is a major player in various inflammation-associated pathologies such as lung injury, viral and nonviral liver diseases, kidney fibrosis, hernia, and vascular disorders. Besides, type III collagen together with type I collagen are the main constituents of the interstitial matrix.

Collagen is essential for having a healthy and smooth skin. The layer of skin responsible for wrinkles is dermis, which is made up of blood vessels, sebaceous glands and hair follicles. Collagen is necessary for the support and elasticity of the dermis. Collagen production naturally decreases with the age, causing in the skin the appearance of wrinkles, scarring and sagging skin. When the deficiency of collagen is in the muscles, muscle pain and soreness is experienced; while if the collagen deficiency is in the cartilage it leads to joint pain. In addition, diseases or conditions that mediate by a collagen degeneration also affect the skin, the muscles and/or the cartilages. This collagen degeneration can be caused by either environmental factors such as sun exposure or by some connective tissue diseases, such as rheumatic fever, rheumatoid arthritis and lupus among others.

When the collagen deficiency is affecting the skin, it may be treated with collagen injections. The collagen injection treatment involves the injection of purified animal/cadaver-derived collagen under the skin of the affected area. Meanwhile, when the collagen deficiency affects the organs, then the treatment involves the ingestion of collagen supplements (available in liquid and pill form). In addition, collagen supplements may also prevent collagen deficiencies from developing them. However, prescription drugs used for collagen supplementing may have side effects derived from its origin (animal or cadaver-derived collagen) such as allergic reaction.

Thus, from what it is known in the state of the art, there is still the need to develop new compounds for the treatment of a disease or condition mediated by a filaggrin or collagen deficiency.

SUMMARY OF INVENTION

Inventors have found that caprylic and capric triglycerides allow increasing the expression of the matrix proteins filaggrin and collagen and therefore, the topical administration of a specific amount of caprylic and capric triglycerides is useful as an active ingredient for the treatment of a disease or condition mediated by a filaggrin or collagen deficiency.

Further, inventors have also found that caprylic and capric triglycerides in combination with other active ingredients such as melatonin or a derivative thereof are also useful as an active ingredient for the treatment of a disease or condition mediated by a filaggrin or collagen deficiency.

Thus, the first aspect of the invention refers to caprylic and capric triglycerides for use in the treatment of a disease or condition mediated by filaggrin or collagen deficiency, wherein the treatment comprises the topical application of a therapeutically effective amount of the caprylic and capric triglycerides.

And, the second aspect of the invention refers a topical composition for use in the treatment of a disease or condition mediated by a filaggrin or collagen deficiency, wherein the treatment comprises the topical application of the composition which comprises an effective amount of the caprylic and capric triglycerides from 0.1 to 70% by weight of the total weight of the composition, together with one or more appropriate topical acceptable excipients or carriers It is also part of the invention the caprylic and capric triglycerides in combination with melatonin or a derivative thereof, or a composition containing them, for use in the treatment of a disease or condition mediated by filaggrin or collagen deficiency.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For purposes of the present invention, any ranges given include both the lower and the upper end-points of the range. Ranges given, such as temperatures, times, and the like, should be considered approximate, unless specifically stated.

The terms "percentage (%) by weight" or "% by weight" are used interchangeably and they refer to the percentage of each ingredient of the composition in relation to the total weight.

As mentioned above, the first aspect of the invention refers to the use of a therapeutically effective amount of the caprylic and capric triglycerides for the treatment of a disease or condition mediated by a filaggrin or collagen deficiency.

The term "therapeutically effective amount" as used herein, refers to the amount of an active ingredient for instance caprylic and capric triglycerides that, when administered, is sufficient to prevent development of, or alleviate to some extent, one or more of the symptoms of the disease which is addressed. The particular dose of the active ingredient administered according to this invention will be determined by the particular circumstances surrounding the case, including the compound administered, the route of administration, the particular condition being treated, and the similar considerations.

For purposes of the present invention, the terms "caprylic and capric triglyceride", "caprylic/capric triglyceride" and the abbreviature "CCT" have the same meaning and they are used interchangeably. In particular, CCT is an oily liquid made of a mixed ester composed of caprylic and capric fatty acids obtained by the esterification of glycerol (plant sugars) with a mixture of caprylic (C:8) and capric (C:10) fatty acids from coconut or palm kernel oils. Caprylic/capric triglycerides are commercially available with the trademark Miglyol 812 among others.

In an embodiment, the caprylic and capric triglycerides for use of the present invention is one wherein the disease or condition is mediated by a filaggrin deficiency, particularly selected from the group consisting of psoriasis, atopic dermatitis and ichthyosis vulgaris.

In an embodiment, the caprylic and capric triglycerides for use of the present invention is one wherein the disease or condition is mediated by a collagen deficiency, particularly selected from the group consisting of skin aging and skin photoaging.

As it is shown in the examples of the present invention, caprylic and capric triglycerides promotes the expression (production) of filaggrin or collagen, and therefore, it is useful for the treatment of a disease or condition mediated by a filaggrin or collagen deficiency. Thus, this aspect could be also formulated as the use of the caprylic and capric triglycerides as defined above for the preparation of a medicament for the treatment of a disease or condition mediated by a filaggrin or collagen deficiency, wherein the treatment comprises the topical application of a therapeutically effective amount of the caprylic and capric triglycerides. It also relates to a method for the treatment of a mammal suffering or is susceptible to suffer from a disease or condition mediated by a filaggrin or collagen deficiency, wherein the method comprises administering to said mammal a therapeutically effective amount of caprylic and capric triglycerides, together with one or more pharmaceutically acceptable excipient or carrier.

In an embodiment, the caprylic and capric triglycerides for use of the present invention is one wherein the treatment comprises the topical application of the caprylic and capric triglycerides in combination with melatonin or a derivative thereof. In an embodiment, the caprylic and capric triglycerides for use of the present invention is one wherein the treatment comprises the topical application of the caprylic and capric triglycerides in combination with a therapeutically effective amount of melatonin or a derivative thereof.

For purposes of the present invention, the term "melatonin" is the Nonproprietary name of the "N-acetyl-5-methoxy tryptamine" with CAS registry number 73-31-4 having the following formula:

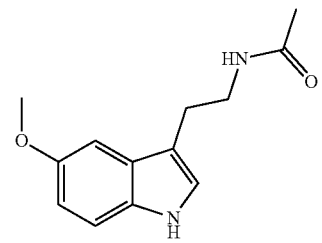 [SMILES: COc1ccc2[nH]cc(CCNC(C)=O)c2c1]

The term "melatonin and derivative thereof" refers to a compound having the following formula:

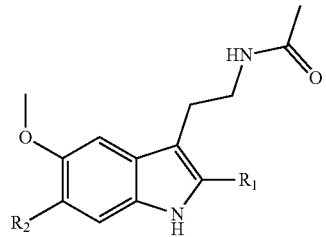

wherein each one of $R_1$ and $R_2$ is independently selected from the group consisting of H and halogen. The term "halogen" refers to fluoro, chloro, bromo or iodo.

As mentioned above, the second aspect of the invention refers to a topical composition for use in the treatment of a disease or condition mediated by a filaggrin or collagen deficiency, wherein: the treatment comprises the topical application of the composition which comprises an effective amount of the caprylic and capric triglycerides from 0.1 to 70% by weight of the total weight of the composition, together with one or more appropriate topical acceptable excipients or carriers.

In an embodiment, the composition for use in the treatment of a disease or condition mediated by a filaggrin or collagen deficiency, is one wherein the therapeutically effective amount of the caprylic and capric triglycerides is one wherein the therapeutically effective amount of the caprylic and capric triglycerides is 0.1%, 0.2%, 0.3%, 0.4%, 0.5%, 0.6%, 0.7%, 0.8% 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69% and 70%.

In an embodiment, the composition for use in the treatment of a disease or condition mediated by a filaggrin or collagen deficiency, is one wherein the treatment comprises the topical application of the composition which comprises: from 0.1 to 70% by weight of the caprylic and capric triglycerides and a therapeutically effective amount of melatonin or a derivative thereof as defined above; particularly from 0.004% to 12% by weight of melatonin or a derivative thereof; together with one or more acceptable excipients or carriers.

The term "topical composition" refers to a composition suitable for its "topical application". The term "topical application" refers to an application on the skin, hair, ears, mucous membranes, rectal application, and nasal application, as well as dental or gum application within the oral cavity.

All the embodiments disclosed above for the first aspect of the invention in relation to the disease or condition mediated by filaggrin or collagen deficiency also apply for the composition of the second aspect of the invention.

The term "appropriate topical acceptable" refers to excipients or carriers suitable for use in the preparation of a compositions suitable for being topically applied.

The topical compositions of the invention can be formulated in several forms that include, but are not limited to, solutions, aerosols and non-aerosol sprays, shaving creams, powders, mousses, lotions, gels, sticks, ointments, pastes, creams, shampoos, shower gel, body washes or face washes.

Topical compositions of the present invention can be prepared according to methods well known in the state of the art. The appropriate excipients and/or carriers, and their amounts, can readily be determined by those skilled in the art according to the type of formulation being prepared.

In an embodiment, the topical composition for use of the present invention, is one wherein the appropriate topical excipient or carrier is selected from the group consisting of a skin barrier recovery agent, an hydrating agent, an emollient, an emulsifier, a surfactant, a thickener, an humectant, a pH-regulating agent, an antioxidant, a preservative agent, a vehicle, a chelating agent, an absorbent and a mixture thereof.

The term "hydrating agent" or "moisturizer" or "moisturizing agent" which is herein used interchangeably refers to a material which increases the water content of the skin and helps keep it soft and smooth. Examples of appropriate topical hydrating agent include, but are not limited to, dimethiconol, glycine, hyaluronic acid, sodium hyaluronate crosspolymer, betaine, dimethylsilanol hyaluronate, magnesium stearate, maltitol, maltose, pyrrolidone carboxylic acid (PCA), manganese PCA, sodium PCA, mannitol, trehalose, trilactin, glucose, glutamic acid, hydrolysed *Caesalpinia spinosa* gum, *Caesalpinia spinosa* gum, *Prunus persica* extract, *Prunus serotina* extract, *Echinacea angustifolia* extract, *Echinacea purpurea* extract, methyl gluceth, hydrolysed wheat gluten, erythritol, aluminium stearoyl glutamate, copper acetylmethionate, or ditridecyl dimmer dilinoleate. The amount of hydrating agent in the compositions of the present invention can be from 0.01 to 20%.

The term "skin barrier recovery agent" refers to material whose composition and/or structure are similar to the skin barrier allowing the reparation of its deficiencies. Examples of appropriate topical skin barrier recovery agent include, but are not limited to, ceramides, cholesterol, fatty acids, and precursors of these lipids including cerebrosides, sphingoid bases such as phytosphingosine or sphingosine, or phospholipids including phosphatidylcholine, and agents that promote the synthesis of epidermal lipids like niacinamide, urea, dexpanthenol, and alpha-hydroxyacids including lactic acid among others. The amount of skin barrier recovery agent in the compositions of the present invention can be from 0.1 to 20%.

The term "emollient" agent refers to a material that softens and soothes the skin in order to correct dryness and scaling of the skin, lubricating the skin surface, encouraging skin water retention, and altering product textures. The term "emollient" includes hydrophilic emollients and lipophilic emollients. The term "hydrophilic emollients" refers to emollients soluble in water such as glycerin, sorbitol, and propylene glycol. The term "lipophilic emollients" includes not soluble in water. Examples of appropriate topical emollient agents include, but are not limited to, octyl hydroxystearate, lanolin, caprylic/capric triglyceride, cetyl palmitate, octyldodecanol, cetyl alcohol, isopropyl isostearate, glyceryl dilaurate, isopropyl myristate, palm alcohol, dimethicone, squalane, *Plukenetia volubilis* seed oil, *Butyrospermum parkii* butter, sucrose cocoate, or their mixtures. The amount of emollient agents in the composition of the present invention can be from 0.1 to 35%.

The term "humectant" agent refers to a hygroscopic material which attracts water molecules from the surrounding environment though either absorption or adsorption, preventing the skin from losing moisture. Examples of appropriate topical humectants include, but are not limited to, glycerin, diglycerin, ethylhexylglycerin, glucose, honey, lactic acid, polyethylene glycol, propylene glycol, sorbitol, sucrose, or trehalose. The amount of the humectants in the composition of the present invention can be from 0.1 to 10%.

The term "thickening agent" or "thickener" or "viscosity agent" which is herein used interchangeably refers to a material that increases its viscosity without substantially modifying its other properties. Examples of appropriate topical thickeners include, but are not limited to, cellulose or their derivatives such as hydroxypropyl methylcellulose, polyethylene glycol, microcrystalline cellulose, cetearyl alcohol, alginates, branched polysaccharides, fumed silica, xanthan gum, carbomer, and polyacrylates. The amount of the thickeners in the composition of the present invention can be from 0.1 to 3%.

The term "emulsifying agent" or "emulsifier" which is herein used interchangeably refers to a material that reduces surface tension, promoting the formation of intimate mixtures of non-miscible liquids by altering the interfacial tension. Emulsifier stabilizes an emulsion by increasing its kinetic stability.

The term "surfactant" refers to a material which lowers the surface tension of a liquid and the interfacial tension between two liquids, allowing their easier spreading. Surfactants have a hydrophilic head that is attracted to water molecules and a hydrophobic tail that repels water and simultaneously attaches itself to oil and grease in dirt. These opposing forces loosen the dirt and suspend it in the water, having the ability to remove it from surfaces such as the human skin, textiles, and other solids, when surfactants are dissolved in water.

The topical composition used is formulated preferably as an emulsion. An emulsion is a dispersed system comprising at least two immiscible phases, one phase dispersed in the other as droplets. The above-mentioned emulsifying agents are included to improve stability. When water is the dispersed phase and oil is the dispersion medium, the emulsion is termed a water-in-oil emulsion (w/o). When oil is dispersed as droplets throughout the aqueous phase, the emulsion is termed an oil-in-water emulsion (o/w). Other types of emulsions known in the art are multiple emulsions, such as water-in-oil-in-water emulsions (w/o/w), GELTRAP emulsions, where the aqueous intern phase is gelified and it is covered by the oil phase, and SWOP emulsions, also known as inversion emulsions. The emulsions used are preferably oil-in-water emulsions. Preferably, the emulsions for use in the sense of the present invention are compatible with creams and lotions.

Another topical composition used is formulated preferably as a "surfactant base". A surfactant base is a blend of at least two surfactants. Surfactants are commonly used in cleaning products, breaking up stains and keeping the dirt in the water solution to prevent its re-deposition onto the surface. Surfactants disperse dirt that normally does not dissolve in water, becoming it dispersible in water, and removable with the wash water. The above-mentioned surfactants are included to lower the surface tension. Preferably, surfactant bases for use in the sense of the present invention are compatible with shampoos, shower gel, and body or face washes.

The term "antioxidant" refers to a material that slows or prevents the oxidation of other molecules. Antioxidants include free radical scavengers and reducing agents. Examples of appropriate antioxidants include, but are not limited to, free radical scavengers or reducing agents such as, acetyl cysteine, ascorbic acid, ascorbyl palmitate, butylated hydroxytoluene, green tea extract, caffeic acid, cysteine, tocopherol, ubiquinone, carnosine, propyl gallate, butylated hydroxytoluene (BHT), and their mixtures. The amount of the antioxidants in the composition of the present invention can be from 0.1 to 20%.

The term "pH-regulating" agent refers to acids or bases that can be used to adjust the pH of the finished product to the desired level, without affecting the stability of the solution. Examples of appropriate topical pH-regulating agents include, but are not limited to, acetic acid, lactic acid, citric acid, ethanolamine, formic acid, oxalic acid, potassium hydroxide, sodium hydroxide, triethanolamine, or their mixtures. The amount of the pH-regulating agent in the composition of the present invention can be from 0.01 to 3%.

The term "preservative" refers to a material that prevents or reduces or slows down microbial growth, providing that the stability of the solution is not affected. Examples of appropriate preservative agents include, but are not limited to, benzoic acid, butylparaben, ethylparaben, propylparaben, methylparaben, sorbic acid, potassium sorbate, sodium benzoate, phenoxyethanol, triclosan, or their mixtures. The amount of the preservatives in the composition of the present invention can be from 0.01 to 1.5%.

The term "chelating agent" refers to a material capable of coordinating or binding metal ions such as calcium, magnesium, iron and manganese metal ions. The amount of the chelating agent in the composition of the present invention can be from 0.001 to 0.1%.

The term "absorbent" refers to a material capable of interacting with and retaining a chemical compound having an affinity for the absorbent. The term absorbent can be also any material capable of absorbing moisture, or otherwise removing moisture from a surrounding atmosphere, or any material capable of absorbing or otherwise removing other chemical compounds, such as but not limited to oxygen, carbon dioxide, carbon monoxide and amine complexes, from the atmosphere. Herein, the term absorbent may be used interchangeably with the term dehydrating agent, desiccant or adsorbent. Non-limiting examples of absorbents would include silica gel, desiccant clay, molecular sieves, zeolites or combinations thereof. The amount of the absorbent in the composition of the present invention can be from 0.1 to 5%.

The compositions mentioned above also include a vehicle. Examples of vehicles include, but are not limited to, water, propylene glycol, butylene glycol, ethanol, isopropanol, or silicones. Preferably, the vehicle is water.

Additionally, the compositions of the present invention may contain other ingredients, such as fragrances, parfums, colorants, and other components known in the state of the art for use in topical formulations.

In an embodiment, the topical composition for use of the second aspect of the present invention, is one wherein the composition comprises one or more additional active ingredients; particularly one or more additional active ingredient selected from the group consisting of cannabinoids, bakuchiol, vitamins or a derivative thereof, peptides, alpha hydroxy acids, alpha amino acids, sunscreen active agents and a mixture thereof.

In an embodiment, the topical composition further comprises one or more cannabinoids as additional active ingredients; particularly selected from the group consisting of palmitoylethanolamide and analogues and derivatives thereof.

In an embodiment, the topical composition further comprises one or more vitamins or a derivative thereof as additional pharmaceutical active ingredients; particularly selected from the group consisting of vitamin c and esters thereof, vitamins of group B and derivatives thereof such as vitamin B3 (niacinamide). In an embodiment the topical composition further comprises one or more vitamins or a derivative thereof as additional pharmaceutical active ingredients in an amount from 0.5 to 30% by weight of the composition.

In an embodiment, the topical composition further comprises one or more esters of vitamin C selected from the group consisting of ascorbyl tetraisopalmitate, ascorbyl palmitate, ascorbyl stearate, ascorbyl linoleate and a mixture thereof; particularly ascorbyl tetraisopalmitate. In an embodiment the topical composition further comprises one or more esters of vitamin C as defined above in an amount from 1 to 20% by weight of the composition.

In an embodiment, the topical composition further comprises vitamins of group B. In an embodiment, the topical composition further comprises niacinamide. In an embodiment, the topical composition further comprises niacinamide in an amount from 0.5 to 6% by weight of the composition. For purposes of the present invention, the terms "niacinamide", "nicotinamide", "nicotinic acid amide", "pyridine-3-carboxylic acid amide", "vitamin $b_3$" and "vitamin pp" have the same meaning and are used interchangeable. They refer to the Nonproprietary name of the compound of CAS registry number 98-92-0 having the following formula:

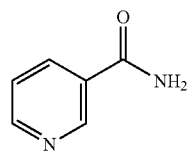

In an embodiment, the topical composition further comprises bakuchiol; particularly in an amount from 0.1 to 1% by weight of the composition. For purposes of the present invention, the term "bakuchiol" is the Nonproprietary name of a natural meroterpene isolated from *P. corylifolia* with the CAS registry number 10309-37-2 having the following formula:

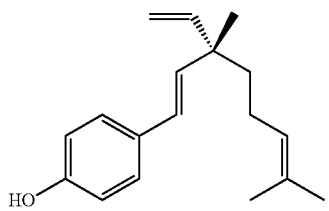 [SMILES: C=C[C@@](C)(/C=C/c1ccc(O)cc1)CCC=C(C)C]

In an embodiment, the topical composition further comprises one or more peptides as additional active ingredients; particularly selected from the group consisting of carnosine, palmitoyl oligopeptide, palmitoyl tetrapeptide-7, tetradecyl aminobutyroylvalylaminobutyric urea trifluoroacetate and other signal peptides, carrier peptides and neurotransmitter peptides. In an embodiment the topical composition further comprises one or more peptides as additional pharmaceutical active ingredients in an amount from 1 to 11% by weight of the composition.

For purposes of the present invention, the terms "carnosine" and "L-carnosine" have the same meaning and they are used interchangeable. These terms are the Nonproprietary name of beta-alanyl-L-histidine with the CAS registry number 305-84-0 having the following formula:

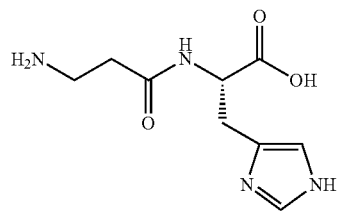 [SMILES: NCCC(=O)N[C@@H](Cc1c[nH]cn1)C(=O)O]

In an embodiment, the topical composition further comprises carnosine; particularly in an amount from 0.01 to 5% by weight of the composition In an embodiment, the topical composition further comprises one or more alpha hydroxy acids as additional active ingredients; particularly selected from the group consisting of glycolic acid, lactic acid and citric acid.

In an embodiment, the topical composition further comprises one or more alpha amino acids as additional active ingredients; particularly selected from the group consisting of betaine, 1 and 5% by weight of the composition; particularly betaine. For purposes of the present invention, the term betaine is the Nonproprietary name of 2-trimethylammonioacetate with the CAS registry number 107-43-7, and having the following formula:

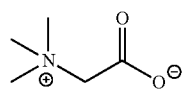

In an embodiment, the topical composition further comprises one or more sunscreen active agents as additional pharmaceutical active ingredients. The term "sunscreen active agent", as used herein, relate to materials, singly or in combination, that are regarded as acceptable for use as active sun screening ingredients based on their ability to absorb, scatter, or reflect ultraviolet (UV) radiation. Such compounds are generally described as being UVA, UVB, or UVA/UVB active agents. Particularly, the "sunscreen organic active agent" refers to organic chemical compounds, singly or in combination, that are regarded as acceptable for use as active sun screening ingredients based on their ability to mostly absorb ultraviolet (UV) radiation. Such compounds are generally described as being UVA, UVB, or UVA/UVB active agents.

In an embodiment, the topical composition for use of the second aspect of the present invention, is one comprising:
from 55 to 70% by weight of the caprylic and capric triglycerides;
from 0.004 to 1% by weight of melatonin or a derivative thereof as defined in claim 3;
from 0.1 to 1% by weight of bakuchiol; and
from 1 to 20% by weight of vitamin c or a derivative thereof
being the sum of the ingredients 100% by weight.

In an embodiment, the topical composition for use of the second aspect of the present invention, is one comprising:
from 55 to 70% by weight of the caprylic and capric triglycerides;
from 0.004 to 1% by weight of melatonin or a derivative thereof as defined in the present invention;
from 0.1 to 1% by weight of bakuchiol;
from 1 to 11% by weight of vitamin c or a derivative thereof; and
from 20 to 30% by weight of emollients;
being the sum of the ingredients 100% by weight.

In an embodiment, the topical composition for use of the second aspect of the present invention, is one wherein the emollients is selected from the group consisting of isodecyl neopentanoate, dimethicone, hydrogenated polyisobutene, octyldodecanol and a mixture thereof.

As mentioned above, the second aspect of the invention refers to a pharmaceutical topical composition for use in the treatment of a disease or condition mediated by a filaggrin or collagen deficiency, wherein: the treatment comprises the topical application of a pharmaceutical composition which comprises a therapeutically effective amount of the caprylic and capric triglycerides from 0.1 to 70% by weight, together with one or more pharmaceutically acceptable excipients or carriers. The composition comprising caprylic and capric triglycerides of the second aspect of the invention promotes the expression (production) of filaggrin or collagen. This aspect could be also formulated as the use of the topical pharmaceutical composition as defined above for the preparation of a medicament for the prophylaxis and/or treatment of a disease or condition mediated by a filaggrin or collagen deficiency, wherein: the treatment comprises the topical application of the pharmaceutical composition of the invention which comprises a therapeutically effective amount of the caprylic and capric triglycerides from 0.1 to 70% by weight. It also relates to a method for the treatment of a mammal suffering or is susceptible to suffer from a disease or condition mediated by a filaggrin or collagen deficiency, wherein the method comprises administering to said mammal a therapeutically effective amount of the topical pharmaceutical composition of the present invention.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

1. Compositions of the Present Invention 1.1. Example 1—Night Emulsion

A. Composition
The emulsion composition is as follows

| Component no | INCI Name (Tradename) | FUNCTION | Amount (% w/w) |
|---|---|---|---|
| 1 | Aqua | Solvent | 69.9 |
|   | Alcohol denat. | | |
|   | Disodium EDTA | Chelating agent | |
|   | Propanediol | Humectant | |
|   | caprylyl glycol | | |
|   | butylene glycol | | |
|   | pentylene glycol | | |
|   | glycerine | | |
|   | Polysorbate 20 | Surfactant | |
|   | Ammonium acryloyldi-methyltaurate/vp copolymer | Thickener | |
|   | Carbomer | | |
|   | Acrylates/c10-30 alkyl acrylate crosspolymer | | |
| 2 | Caprylic/capric triglyceride | Active ingredient | 30.1 |
|   | Stearyl alcohol | Emollient | |
|   | Isodecyl neopentanoate | | |
|   | Dimethicone | | |
|   | Octyldodecanol | | |
|   | Tridecyl trimellitate | | |
|   | Tridecyl stearate | | |
|   | Neopentyl glycol dicaprylate/dicaprate | | |
|   | Hydrogenated polyisobutene | | |
|   | Olus oil | | |
|   | Antioxidant | | |
|   | Emulsifying | | |
| 3 | Ci 19140 | Cosmetic colorant | |
|   | Ci 15985 | | |
|   | Silica | Absorbent | |
|   | Tetradecyl aminobutyroyl-valylaminobutyric urea trifluoroacetate | Active | |
|   | Magnesium chloride | | |
|   | Sodium hyaluronate crosspolymer | | |
|   | Panthenol | | |
|   | Betaine | | |
|   | Niacinamide | | |
|   | Melatonin | | |
|   | Carnosine | | |
|   | Peptide complex | | |
|   | Helichrysum italicum extract | | |
|   | Preservative | Preservative | |
|   | Parfum | Parfum | |
| Total weight of the composition | | | 100 |

In the above composition, the amount of caprylic and capric triglycerides is 2% by weight, the carnosine is 0.5% by weight, of the niacinamide is 3% by weight, of the melatonin is 0.05% by weight and of the betaine is 1% by weight.

B. Preparation Process
A night cream having the composition indicated in the table below was prepared according to a process comprising the following steps:

B.1. Preparation of Phases
Aqueous Phase (1): Components from phase (1) were added in the main container one after the other under stirring until having a homogeneous solution.
Oily Phase (2): In an auxiliary vessel, components from phase (2) were added and melted.
Phase (3): In an auxiliary vessel, components from phase (3) were added one after the other under stirring until having a homogeneous mixture.

B.2. Process for Manufacturing the Emulsion:
Step 1: Phase (2) was added to phase (1) and then the resultant mixture was mixed until having an emulsion; and
Step 2: Phase (3) was added to the resulting emulsion obtained in step 1 to obtain the final emulsion.

1.2. Example 2

A. Composition

| Component no | INCI Name (Tradename) | function | Amount (% w/w) |
|---|---|---|---|
| 0 | Caprylic/capric triglyceride | active | 62.5 |
| 1 | Melatonin | active | |
| 2 | Preservative system | | |
| 3 | Squalane | Emollient | |
| 4 | Dicaprylyl carbonate, tocopherol | Emollient | 37.5 |
| 5 | Bakuchiol | active | |
| 6 | Antioxidant system | | |
| 7 | Parfum | | |
| 8 | Alcohol denat. | solvent | |
| 9 | Aqua | | |
| 10 | Ascorbyl tetraisopalmitate (vitamin C derivative) | active | |
| Total weight of the composition | | | 100 |

In the above composition, the amount of caprylic and capric triglycerides is 55% by weight, of the melatonin is 0.05% by weight, of bakuchiol is 0.3% by weight and of vitamin C derivative is 8% by weight.

B. Preparation Process
Adding components 0 to 10 one by one under agitation until obtaining a homogeneous mixture.

2. Determination of Matrix Proteins 2.1. Samples

Normal human dermal fibroblast growth supplement was purchased from PAN Biotech.
Cell culture media including Dulbecco's modified Eagle's medium (DMEM, fetal bovine serum (FBS) and penicillin-streptomycin were obtained from Gibco BRL.
Normal human keratinocyte growth supplement was purchased from CELLnTech.
For the determination of collagen III into fibroblast cultures:
Fibroblast treated with 500 µl of caprylic/capric triglycerides at a concentration of 0.1%, 0.2%, 1% and 2% expressed as g/100 mL.
Blank: Fibroblast P8-9
For the determination of filaggrin into keratinocyte cultures:

Keratinocytes treated with 500 μl of caprylic/capric triglycerides at a concentration of 0.1%, 0.2%, 1% and 2% expressed as g/100 mL.

Blank: Keratinocytes

The amount of the active ingredients (for instance caprylic acid and capric triglycerides) used in the in-vitro assays for the determination of collagen III into fibroblast cultures and filaggrin into keratinocytes cultures is equivalent to the amount of active ingredient that reach the fibroblast and keratinocytes after the topical application of the composition of the invention on the skin.

2.2. Apparatus

Nikon Ti—S microscope (metamorph).
The Incucyte (ESSEN BioScience).

2.3. Antibodies

Purified freeze-dried antibody to human type III collagen; Ref: 20311 (novotec)
Anti-filaggrin antibody; Ref: PAJ103hu01 (cloud-cloud)

2.4. Method

Normal human dermal fibroblast growth supplement was purchased from PAN Biotech.
Cell culture media including Dulbecco's modified Eagle's medium (DMEM, fetal bovine serum (FBS) and penicillin-streptomycin were obtained from Gibco BRL.
Normal human keratinocyte growth supplement was purchased from CELLnTech.

2.5. Cell Culture

Fibroblasts
  Culture: Primary Human dermal face fibroblasts (HDF) were isolated from human dermal face tissue removed at the time of the women facelifts (45 years) and were used at passage 2-15. The HDF were maintained in DMEM containing 10% FBS and 1% penicillin-streptomycin.
  Human fibroblasts: face epidermal fibroblasts of 40-year-old patient
Keratinocytes
  Culture: Primary Human epidermal adult keratinocytes (HEK) isolated from human epidermal tissue were purchased from CELLnTec advanced cell systems. The HEK were maintained in CnT-basal Medium supplemented with Cnt-57-S(CELLnTEC).
Cells were maintained in a humidified chamber at 5% $CO_2$ and 37° C. Medium was changed every 4 days.
  Human keratinocytes: epidermal keratinocytes progenitors, pooled: (HPEKp; CellnTec).

2.6. Immunostaining

For immunostaining, cultures cells in a well were washed with PBS and fixed with 4% paraformaldehyde for 10 min, after washing with PBS, the fixed cells were permeabilized with 0.2% Triton-X100 in PBS for 10 min. Following two washes with PBS, the cells were blocked with 1% BSA+ 0.1% Tween 20 in PBS at 37° C. for 60 min. the cells were incubated with the primary antibodies in blocking buffer at 37° C. overnight. After washing, the following secondary antibodies were applied: Alexa Fluor 488 goat anti-mouse immunoglobulin G (IgG) (Molecular Probes) and Alexa Fluor 488 goat anti-rabbit IgG (Molecular Probes). The cells were incubated with the secondary antibodies in blocking buffer at room temperature for 2 hours. After washing with PBS, the cells were incubated with DAPI in room temperature for 10 min. Fluorescence images were obtained using a Nikon Ti—S microscope with band filter (DAPI/GFP).

2.7. Determination of Collagen III into Fibroblast Cultures

The Table below shows the increase of production of collagen III in fibroblasts by the use of CCT. The amount of collagen III expressed was increased by 1.1, 1.8, 2.3 and 2.5-fold with increasing concentrations of CCT as described in the Table below, wherein the amount of CCT is expressed as grams of CCT per 100 mL:

| CCT (%) | Expression of collagen III in fibroblasts |
| --- | --- |
| 0 (blank) | 57558.6 |
| 0.1 | 62627.1 |
| 0.20 | 102986.8 |
| 1 | 130587.6 |
| 2 | 141063.6 |

As it is shown in the above results, the CCT allows increasing the production of collagen, particularly collagen III, in fibroblasts. It is advantageous because CCT can be useful for ameliorating or treating a disease or condition mediated with a collagen deficiency caused by a reduction of the production of collagen or with an increase of collagen degeneration.

2.8. Determination of Filaggrin into Keratinocytes Culture

The Table below shows the increase of production of filaggrin in fibroblasts by the use of CCT. The amount of filaggrin expressed was increased by 1.7 and 2.8-fold with increasing concentration of CCT as described in the Table below and the amount of CCT is expressed as grams of CCT per 100 mL:

| CCT (%) | Expression of filaggrin in keratinocytes |
| --- | --- |
| 0 (blank) | 38795.3 |
| 1.00 | 65175.8 |
| 10 | 108008.1 |

As it is shown in the above results, the CCT allows increasing the production of filaggrin in keratinocytes. It is advantageous because as filaggrin plays a key role in maintaining an effective skin barrier against the environmental conditions, CCT can be useful as skin recovery agent for enhancing/repairing the function and health of skin. In particular, CCT is useful for ameliorating or treating a disease or condition mediated with a filaggrin deficiency caused by a reduction of the production of filaggrin or with an increase of filaggrin degeneration.

The invention claimed is:
1. A method of treatment of a disease or condition mediated by filaggrin or collagen deficiency, wherein the method comprises topical application of a therapeutically effective amount of caprylic and capric triglycerides.

2. The method according to claim 1, wherein the disease or condition mediated by a filaggrin or collagen deficiency is selected from the group consisting of psoriasis, atopic dermatitis, ichthyosis vulgaris, skin aging, and skin photoaging.

3. The method according to claim 1, wherein the method comprises topical application of the caprylic and capric triglycerides in combination with melatonin or a derivative thereof having the following formula:

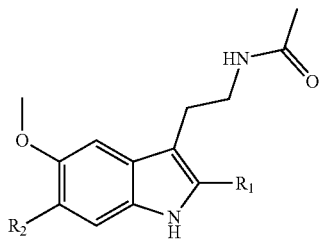

wherein each one of $R_1$ and R2 is independently selected from the group consisting of H and halogen.

4. The method according to claim 1, wherein the method comprises topical application of a composition comprising the caprylic and capric triglycerides, together with one or more appropriate topical acceptable excipients or carriers; and
    wherein the caprylic and capric triglycerides are from 0.1 to 70% by weight of the total weight of the composition.

5. The method according to claim 3, wherein the method comprises topical application of a composition comprising the caprylic and capric triglycerides, the melatonin or the derivative thereof, together with one or more appropriate topical acceptable excipients or carriers;
    wherein the caprylic and capric triglycerides are from 0.1 to 70% by weight of the total weight of the composition; and
    wherein the melatonin or the derivative thereof is from 0.004% to 12% by weight of the total weight of the composition.

6. The method according to claim 4, wherein the disease or condition mediated by a filaggrin or collagen deficiency is selected from the group consisting of psoriasis, topical dermatitis, ichthyosis vulgaris, skin aging, and skin photoaging.

7. The method according to claim 4, wherein the appropriate topical acceptable excipient or carrier is selected from the group consisting of an hydrating agent, an emollient, an emulsifier, a surfactant, a thickener, an humectant, a pH-regulating agent, an antioxidant, a preservative agent, a vehicle, a chelating agent, an absorbent, and a mixture thereof.

8. The method according to claim 4, wherein the composition comprises one or more additional active ingredients.

9. The method according to claim 8, wherein the additional active ingredient is selected from the group consisting of cannabinoids, bakuchiol, vitamins or a derivative thereof, peptides, alpha hydroxy acids, alpha amino acids, sunscreen active agents, and a mixture thereof.

10. The method according to claim 4, wherein the composition comprises the caprylic and capric triglycerides from 55% to 70% by weight of the total weight of the composition, together with one or more appropriate topical acceptable excipients or carriers.

11. The method according to claim 5, wherein the composition comprises:
    from 55 to 70% by weight of the caprylic and capric triglycerides;
    from 0.004 to 1% by weight of melatonin or the derivative thereof;
    from 0.1 to 1% by weight of bakuchiol;
    from 1 to 20% by weight of vitamin C or a derivative thereof; and
    one or more appropriate topical acceptable excipients or carriers.

12. The method according to claim 11, wherein the composition further comprises from 20 to 30% by weight of emollients.

13. The method according to claim 11, wherein the derivative of vitamin C is ascorbyl tetraisopalmitate.

14. The method according to claim 4, wherein the composition comprises the therapeutically effective amount of the caprylic and capric triglycerides from 1% to 10% by weight of the total weight of the composition, together with one or more appropriate topical acceptable excipients or carriers.

15. The method according to claim 3, wherein the composition comprises:
    from 1 to 10% by weight of the caprylic and capric triglycerides;
    from 0.004 to 1% by weight of melatonin or the derivative thereof;
    from 0.05 to 1% by weight of carnosine;
    from 0.5% to 6% by weight of niacinamide;
    from 0.5% to 5% by weight of betaine; and
    one or more appropriate topical acceptable excipients or carriers.

16. The method according to claim 2, wherein the method comprises topical application of the caprylic and capric triglycerides in combination with melatonin or a derivative thereof having the following formula:

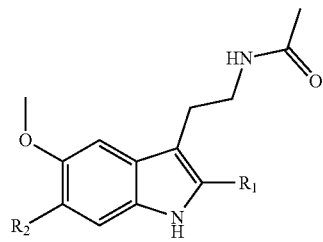

wherein each one of $R_1$ and $R_2$ is independently selected from the group consisting of H and halogen.

17. The method according to claim 5, wherein the disease or condition mediated by a filaggrin or collagen deficiency is selected from the group consisting of psoriasis, topical dermatitis, ichthyosis vulgaris, skin aging, and skin photoaging.

* * * * *